US011250726B2

(12) United States Patent
Barral et al.

(10) Patent No.: US 11,250,726 B2
(45) Date of Patent: Feb. 15, 2022

(54) SYSTEM FOR SIMULATION OF SOFT BODIES

(71) Applicant: Verily Life Sciences LLC, South San Francisco, CA (US)

(72) Inventors: Joëlle K. Barral, Mountain View, CA (US); Gianni Campion, Mountain View, CA (US); Martin Habbecke, Palo Alto, CA (US); Xing Jin, San Jose, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 430 days.

(21) Appl. No.: 16/364,510

(22) Filed: Mar. 26, 2019

(65) Prior Publication Data

US 2019/0362651 A1 Nov. 28, 2019

Related U.S. Application Data

(60) Provisional application No. 62/676,174, filed on May 24, 2018.

(51) Int. Cl.
| | |
|---|---|
| *G09B 23/28* | (2006.01) |
| *G06N 3/08* | (2006.01) |
| *G09B 23/30* | (2006.01) |
| *A61B 34/10* | (2016.01) |
| *G16H 50/50* | (2018.01) |
| *A61B 34/30* | (2016.01) |

(52) U.S. Cl.
CPC ............. *G09B 23/285* (2013.01); *G06N 3/08* (2013.01); *G09B 23/30* (2013.01); *A61B 34/10* (2016.02); *A61B 34/30* (2016.02); *G16H 50/50* (2018.01)

(58) Field of Classification Search
CPC ................................ G09B 23/28; G09B 23/30
See application file for complete search history.

(56) References Cited

U.S. PATENT DOCUMENTS

| 7,225,404 B1 | 5/2007 | Zilles et al. |
| 9,283,675 B2 | 3/2016 | Hager et al. |
| | (Continued) | |

OTHER PUBLICATIONS

Nurnberger et al., A Problem Specific Recurrent Neural Network for the Description and Simulation of Dynamic Spring Models, Neural Networks Proceedings, May 4, 1998. (Year: 1998).*

(Continued)

*Primary Examiner* — Kurt Fernstrom
(74) *Attorney, Agent, or Firm* — Christensen O'Connor Johnson Kindness PLLC

(57) ABSTRACT

A simulator for simulating soft body deformation includes a display system, a user interface, and a controller. The controller includes one or more processors coupled to memory that stores instructions that when executed cause the system to perform operations. The operations include generating a simulated soft body having a shape represented, at least in part, by a plurality of nodes. The operations further include determining, with at least a first machine learning model, a displacement of individual nodes included in the plurality of nodes in response to a simulated force applied to the simulated soft body. The operations further include rendering a deformation of the simulated soft body in substantially real time in response to the simulated force based, at least in part, on the displacement.

24 Claims, 8 Drawing Sheets

(56) References Cited

U.S. PATENT DOCUMENTS

| | | | | |
|---|---|---|---|---|
| 9,601,030 | B2* | 3/2017 | Ratcliffe | G09B 23/28 |
| 9,711,066 | B2* | 7/2017 | Van Dinther | G09B 9/00 |
| 9,788,905 | B2* | 10/2017 | Avisar | G16H 40/60 |
| 9,875,339 | B2* | 1/2018 | Namer Yelin | G16H 50/50 |
| 10,311,978 | B2* | 6/2019 | Mansi | G06F 30/20 |
| 10,912,619 | B2* | 2/2021 | Jarc | A61B 90/361 |
| 10,987,176 | B2* | 4/2021 | Poltaretskyi | A61B 34/10 |
| 2004/0009459 | A1* | 1/2004 | Anderson | G06T 19/00 434/262 |
| 2008/0193904 | A1* | 8/2008 | Santhanam | G09B 23/28 434/272 |
| 2010/0217336 | A1* | 8/2010 | Crawford | G16H 50/50 606/86 R |
| 2012/0178069 | A1 | 7/2012 | McKenzie et al. | |
| 2014/0199673 | A1* | 7/2014 | Jian | G06F 3/016 434/262 |
| 2014/0324400 | A1* | 10/2014 | Quam | G06T 17/20 703/2 |
| 2017/0328716 | A1* | 11/2017 | Ma | G06K 9/6269 |
| 2017/0330075 | A1 | 11/2017 | Tuysuzoglu et al. | |

OTHER PUBLICATIONS

Liang et al., A Deep Learning Approach to Estimate Stress Distribution: a fast and accurate surrogate of finite-Jement analysis, Journal of the Royal Society. Interface, vol. 15, No. 138, Jan. 1, 2018 (Year: 2018).*

Nurnberger et al., A Problem Specific Recurrent Neural Network for the Description and Simulation of Dynamic Spring Models, Neural Networks Proceedings, May 4, 1998, pp. 472,468.

Anonymous, Deep Learning—Wikipedia, May 22, 2018.

Ruder, An Overview of Multi-Task Learning for Deep Learning, May 3, 2018, p. 3, paragraph 3.

Liang et al., A Deep Learning Approach to Estimate Stress Distribution: a fast and accurate surrogate of finite-element analysis, Journal of the Royal Society Interface, vol. 15, No. 138, Jan. 1, 2018, p. 20170844.

Song et al., Generalization Tower Network: A Novel Deep Neural Network Architecture for Multi-Task Learning, Arix.Org, Cornell University Library, Oct. 27, 2017.

International Search Report and Written Opinion, dated Jul. 24, 2019, of corresponding International Application No. PCT/US2019/032530, 14 pages.

Boscaini, D. et al., "Learning Sharpe Correspondence with Anisotropic Convolutional Neural Networks", 30th Conference on Neural Information Processing Systems, 2016, Barcelona, Spain, 9 pages.

Morooka, K. et al., "A Method for Constructing Real-Time FEM-based Simulator of Stomach Behavior with Large-Scale Deformation by Neural Networks", SPIE Medical Imaging Conference, 2012, San Diego, California, 7 pages.

Zhong, Y. et al., "A Cellular Neural Network Methodology for Deformable Object Simulation", IEEE Transactions on Information Technology in Biomedicine, vol. 10, No. 4, Oct. 2006, 14 pages.

Han, S. et al., "Deep Neural Networks Show an Equivalent and Often Superior Performance to Dermatologists in Onychomycosis Diagnosis: Automatic Construction of Onychomycosis Datasets by Region-Based Convolutional Deep Neural Network", Retrieved from Internet: <https://journals.plos.org/plosone/article?id=10.1371/journal.pone.0191493> Jan. 18, 2018, 14 pages.

De, S. et al., "A Physics-Driven Neural Networks-based Simulation System (PhyNNeSS) for Multimodal Interactive Virtual Environments Involving nonlinear Deformable Objects", Presence, vol. 20, No. 4, Aug. 2011, 20 pages.

* cited by examiner

SYSTEM FOR SIMULATION OF SOFT BODIES

CROSS-REFERENCE TO RELATED APPLICATIONS

This application claims the benefit of U.S. Provisional Application No. 62/676,174, filed May 24, 2018, which is hereby incorporated by reference in its entirety.

TECHNICAL FIELD

This disclosure relates generally to simulators, and in particular but not exclusively, relates to robot-assisted surgical simulators.

BACKGROUND INFORMATION

Robotic or computer assisted surgery uses robotic systems to aid in surgical procedures. Robotic surgery was developed as a way to overcome limitations (e.g., spatial constraints associated with a surgeon's hands, inherent shakiness of human movements, and inconsistency in human work product, etc.) of pre-existing surgical procedures. In recent years, the field has advanced greatly to limit the size of incisions, and reduce patient recovery time.

In the case of open surgery, robot-assisted instruments may replace traditional tools to perform surgical motions. Feedback-controlled motions may allow for smoother surgical steps than those performed by humans. For example, using a surgical robot for a step such as rib spreading may result in less damage to the patient's tissue than if the step were performed by a surgeon's hand.

Even with robotic or computer assisted surgery, complications during surgery may occur. The surgeon, for example, may incorrectly identify an anatomical structure due to the sometimes limited view of a surgical site. In another example, the surgeon may inadvertently nick or cut the anatomical structure with the instrument. Furthermore, the mechanical operation of the robotic system, or even the operation of traditional surgical tools, may require a significant degree of training to ensure competency. Thus, realistic and robust training for the surgeon may help reduce the risk of complications occurring during surgery.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
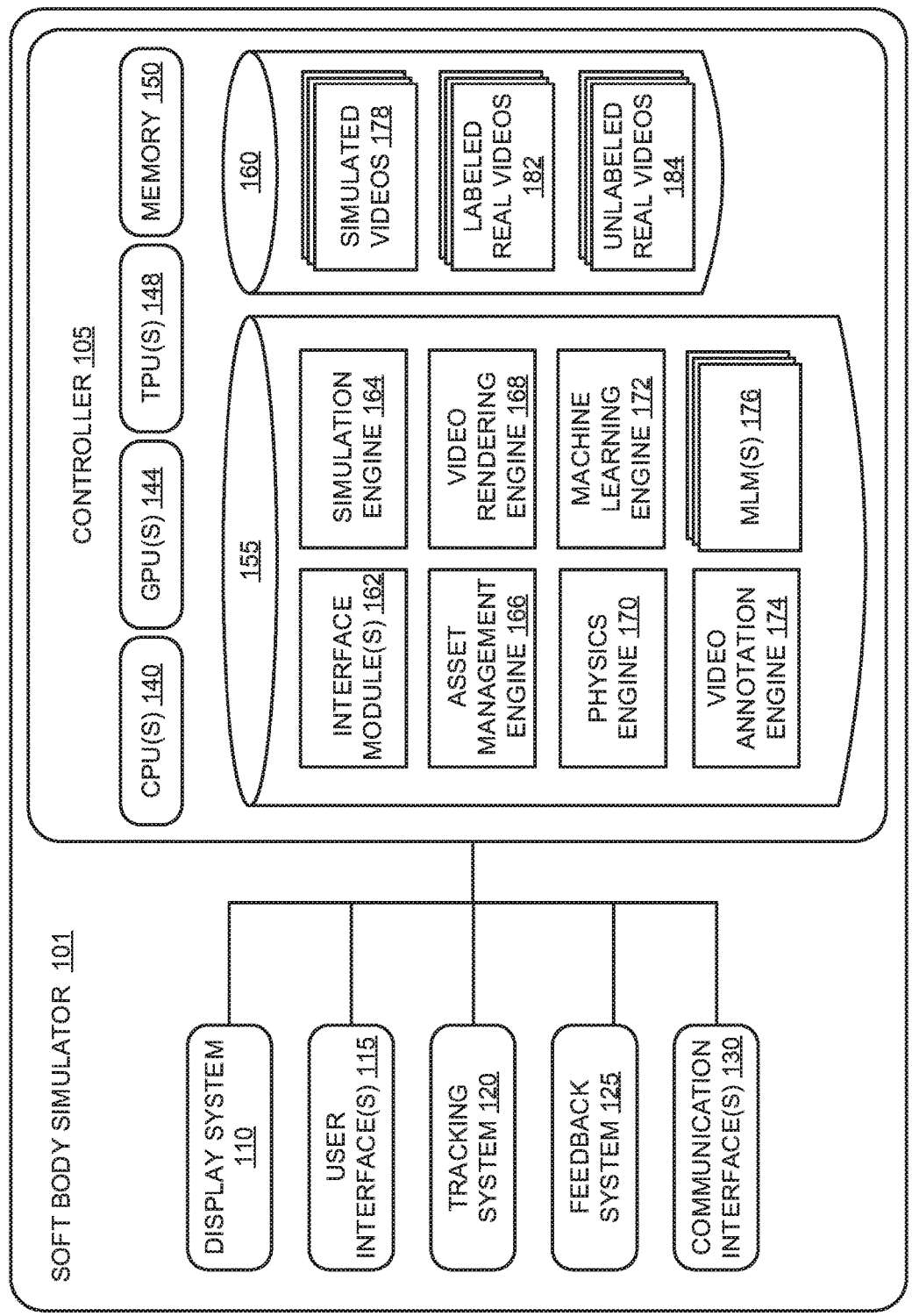
FIG. 1 illustrates a block diagram for a soft body simulator adapted to render a deformation of a simulated soft body, in accordance with an embodiment of the present disclosure.

Embodiments of a system and method for simulation of soft body deformation provided, at least in part, by a machine learning model are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein are embodiments of a soft body simulator (e.g., a surgical simulator) that may be utilized by a medical practitioner (e.g., surgeon, medical student, technician, and the like) for improving or refreshing surgical skills for various surgical techniques and/or scenarios. In the same or other embodiments, non-medical practitioners (e.g., engineers, medical device manufacturers, and the like) may also utilize the soft body simulator for various purposes (e.g., training, testing, product demonstration, and the like) in which simulation of a deformable soft body is desired. The soft body simulator provides accurate and realistic simulation of deformable soft bodies in real time, which have traditionally been considered computationally expensive due to the nonlinearity of soft body deformation and necessary fine spatial resolution to achieve realistic visual results. The deformations are generated in real time such that a user may not notice response lag/delay between when an action is performed to cause deformation of the deformable soft body and when the surgical simulator generates, renders, and displays the response (e.g. the deformation) of the simulated soft body. In some embodiments, the surgical simulator may take into account the skill of the surgeon. For example, the surgical simulator may increase the complexity of the simulation to match the proficiency of the surgeon as the surgeon's proficiency increases over time. To lower the burden of the computational cost, embodiments of the soft body simulator utilize one or more machine learning models to interpret the complex relationship between user interaction (e.g., by a medical practitioner utilizing the soft body simulator) and the reaction of a simulated soft body (e.g., deformation of the simulated soft body in response to the user interaction). Advantageously, the use of one or more machine learning models may allow for increased simulated soft body quality (e.g., pixel resolution, number of nodes representing the simulated soft body, etc.) within a predefined computational cost threshold.

In some embodiments, the one or more machine learning models of the soft body simulator are neural networks which are trained to approximate nonlinear functions (e.g., deformation of the simulated soft body) by providing samples of the relationship between inputs (e.g. a simulated force applied to the simulated soft body corresponding to the user interaction) and outputs (e.g. the deformation of the simulated soft body in response to the simulated force). The neural networks may accelerate the rendering of nonlinear deformation of the simulated soft body in real time for use in simulated surgical fields for laparoscopic applications, robotic applications, or any other application where the simulation of soft bodies with complex material properties is desired. More specifically, the neural networks are trained on the complex relationship between user interactions and soft body simulated reactions.

In one embodiment, the simulated soft body may be represented as a mesh (e.g., polygon mesh, volumetric mesh, and the like) including a plurality of nodes. Each of the plurality of nodes may be interconnected with adjacent nodes and correspond to vertices, edges, and/or faces that define the shape of the simulated soft body. In one embodiment, the shape of the simulated soft body corresponds to the geometric boundary that defines the structure of the simulated soft body in two or three dimensions. In some embodiments, the simulated soft body may have a shape defined by volumetric or voxelized datasets, which may also include a plurality of nodes.

In the same or other embodiments, rendering the deformation of the simulated soft body in response to the simulated force (e.g., determined via user interaction) may be separated into three or more components which are approximated by the one or more machine learning models (e.g., neural networks). The three components include a local response in which a neural network determines static computation of the force displacement properties of the mesh. In other words, the machine learning model determines a displacement of individual nodes included in the plurality of nodes in response to the simulated force. The local response is a point-wise interaction between the simulated force and one or more of the individual nodes included in the plurality of nodes.

A second component included in the three components that may be approximated by the one or more machine learning models is a global response in which the same or a different neural network determines static computation of the force, stress, and/or strain distribution of each individual node included in the plurality of nodes of the simulated soft body (e.g., a response distribution map) based on the position of the nodes in the mesh. For example, the position of the individual nodes may be changed (e.g., the displacement) based on the simulated force applied to the simulated soft body. The position of the individual nodes may result in internal or external forces, stresses, and/or strains being applied to the simulated soft body. For example, each of the individual nodes may have an equilibrium position or state, that when disrupted (e.g., in response to an external force) results in a local stress, force, or strain being applied to the simulated soft body. In some embodiments, a dynamic simulation of the soft body may be generated in response to the force, stress, and/or strain distribution of the simulated soft body by integrating the equations of motion into the system to determine, for example, velocity of individual nodes.

A third component included in the three components which may be approximated by one or more machine learning models is a dynamic response in which full simulation of the simulated soft body and the response of the simulated soft body (e.g., deformation) to the simulated force is rendered. The dynamic response includes the one or more machine learning models being given a sequence of inputs from the user (e.g., corresponding to the simulated force). The one or more machine learning models then output (e.g., compute) the evolution of the system (e.g., the simulated soft body) over a period of time (e.g., until a static equilibrium state of the simulated soft body is reached). In some embodiments, the third component may work in conjunction with the first and second components (e.g., the local response and global response) for determining the dynamic response of the simulated soft body.

FIG. 1 illustrates a system 100 for a soft body simulator 101 adapted to render a deformation of a simulated soft body, in accordance with an embodiment of the disclosure. In the following embodiments, the system 100 will be described in the context of a soft body simulator 101 incorporated as a surgical simulator. The surgical simulator provides medical practitioners a simulated environment (e.g., a simulated surgical scenario representing invasive or non-invasive robotic-assisted surgery) in which the medical practitioner may train or improve their surgical techniques (e.g., creating an incision, excising a tumor, suturing, and the like) on a simulated soft body (e.g., liver). However, it is appreciated that soft body simulator 101 may also be utilized in non-surgical scenarios (e.g., to simulate deformation of simulated soft bodies).

As illustrated, system 100 includes controller 105, display system 110 (e.g., for rendering the simulation in 2D and/or 3D), user interfaces 115 (e.g., user interface devices, pedals, joysticks, gloves, and the like), tracking system 120, feedback system 125, and communication interfaces 130. Controller 105 includes one or more central processing units (CPU) 140, one or more graphic processing units (GPU) 144, one or more tensor processing units (TPU) 148, memory 150, data store 155, and data store 160 coupled to one another (e.g., via a communication bus). The data store 155 includes one or more interface modules 162, a simulation engine 164, an asset management engine 166, a video rendering engine 168, a physics engine 170, a machine learning engine 172, a video annotation engine 174, and one or more (trained or untrained) machine learning models (MLM) 176. The data store 160 may correspond to a video database (e.g., a surgical video database) and include simulated videos 178 (e.g., simulated surgical videos of the surgical scenario), labeled (e.g., annotated) real videos 182 (e.g., real videos of the surgical scenario), and unlabeled real videos 184 (e.g., real videos of the surgical scenario). It should be appreciated that one or more of the components illustrated in FIG. 1 are optional and need not be present in all embodiments.

As illustrated, the display system 110, the user interfaces 115, the tracking system 120, the feedback system 125, and the communication interfaces 130 are coupled to one another and the controller 105. The controller 105 orchestrates the operation of the soft body simulator 101 in response to one or more inputs from a user (e.g., a medical practitioner) of the soft body simulator 101 and instructions stored within the memory 150 and/or the data store 155. The display system 110 may include one or more displays (e.g., liquid crystal display, organic light emitting diode display, and the like) to display the simulated videos 178, the labeled real videos 182, the unlabeled real videos 184, or the like to the user. In the same or other embodiments, the display system 110 may show the simulation (e.g., of the simulated soft body) to the user in real time or near real time as the simulation is being generated in order to allow the user to perform simulated actions within the simulation of the surgical scenario (e.g., creating an incision, excising a tumor, suturing, and the like). In some embodiments, the simulated actions may correspond to a simulated force being applied to the simulated soft body. The simulated soft body may be deformed in response to the simulated force.

The user interfaces 115 may include interface devices that may be physically manipulated by the user which the soft body simulator 101 correlates as a simulated action (e.g., the simulated force) with a simulated surgical instrument during the simulation. For example, the interface devices may include a touchscreen, a game pad, a mouse, a keyboard, a track pad, a surgical instrument (e.g., graspers, clamps, retractors, scalpels, scissors, staplers, endoscopes, and the like), a foot pedal, a control console, a computer screen, and the like. In some embodiments, the soft body simulator 101 may include the same or similar instruments utilized in robotic assisted surgery as interface devices to provide a realistic simulation experience. The user may physically manipulate the one or more interface devices to cause a change in motion (e.g., position, orientation, velocity, acceleration) of the one or more interface devices which is then tracked by the tracking system 120.

During the simulation, the tracking system 120 records changes in the motion of the one or more interface devices and simulates a corresponding motion of the simulated surgical instrument to allow for the user to perform simulated surgical actions within the simulation. The simulated surgical actions may result in a simulated force being applied to the simulated soft body. Thus the tracking system 120 correlates a physical action (e.g., manipulation of the user interfaces 115) to a simulated force (e.g., applied to the simulated soft body). In some embodiments, the tracking system 120 may include cameras, infrared lights, one or more eye trackers, a watch, other body worn sensors, and the like to record the physical motion of the user (e.g., appendage movement, body movement, head movement, eye movement, and the like). The feedback system 125 may provide feedback (e.g., haptic motion, visual representation, audible cues, and the like) to inform the user of a surgical event (e.g., the simulated instrument contacting the simulated soft body). The feedback system may include one or more speakers, displays, transducers and the like to provide the corresponding feedback.

The communication interfaces 130 are provided to facilitate intercommunication between components of the soft body simulator 101 and external devices. For example, the communication interfaces 130 may include known wired data buses (e.g., USB, Ethernet, etc.) and wireless interfaces (e.g., Bluetooth, WiFi, etc.). In some embodiments, one or more components of the soft body simulator 101 may be remotely located or cloud-based. In a cloud-based architecture, processing (e.g., with the CPUs 140, GPUs 144, and/or TPUs 148) may occur remotely.

As illustrated in FIG. 1, the controller 105 is interconnected with the other components of the soft body simulator 101 to control and choreograph their interactions. Processors (e.g., CPUs 140, GPUs 144, TPUs 148, application specific integrated circuits, and the like) control the operations of the soft body simulator 101 via the execution of logic/modules/engines within data store 155 as instructions, which may be stored locally within memory 150 or externally (e.g., memory or data stores communicatively coupled to the soft body simulator 101). The modules 162-176 may be implemented as software logic (e.g., executable software code), firmware logic, hardware logic, or various combinations thereof.

In the illustrated embodiment, the modules 162-176 are utilized to simulate a surgical scenario including a simulated soft body that may be deformed in response to a simulated force corresponding to a user virtually interacting with the simulated soft body. The interface modules 162 control or receive inputs from the user interfaces 115 and the tracking system 120. The simulation engine 164 generates various aspects of the simulation. For example, in one embodiment, the simulation engine 164 generates a simulated soft body (e.g., representative of a liver) having a shape defined by a plurality of nodes (e.g. a polygon mesh). The asset management engine 166 may then determine, based on the specific anatomical feature (e.g., the liver) corresponding to the simulated soft body, a texture to be applied to the simulated soft body for accurate and realistic rendering of the simulated soft body. In the same or other embodiments, the simulation engine 164 may correlate the physical action of the user (e.g., manipulation of the interface devices 115) with the simulated force applied to the simulated soft body. For example, the simulation engine 164 may transform the physical action of the user to a signal which may subsequently be utilized to determine the simulated force being applied to the simulated soft body.

The video rendering engine 168 generates or renders the simulation to display (e.g., via the display system 110) the simulation to the user of the soft body simulator 101 in real time. For example, during the simulation including the simulated soft body, the video rendering engine 168 simultaneously records a simulated surgical video based on the simulation. The video rendering engine 168 may store the simulated surgical videos within data store 160 as simulated videos 178. The physics engine 170 may be utilized for simulations not determined via the machine learning engine 172 (e.g., low computational cost simulations).

The machine learning engine 172 utilizes one or more machine learning models extracted from the database of MLMs 176 to determine the complex relationship between user interactions (e.g., the simulated force corresponding to the physical action of the user applied to the simulated soft body) and a corresponding reaction of the simulated soft body. In some embodiments, different machine learning models of MLMs 176 correspond to different anatomical features or elements. In the same or other embodiments, one or more of the machine learning models from the MLM 176 correspond to a feature or aspect of the deformation of a simulated soft body in response to the simulated force. The MLMs 176 may include various types of neural networks such as feed forward multi-layer deep neural networks (e.g., with multiple towers and/or objectives), recursive neural networks, recurrent neural networks, convolutional neural networks, and the like. In one embodiment, the MLMs 176 includes a convolutional network in non-Euclidean domains for deformable object (e.g., soft body) feature extraction, by treating the mesh as a manifold surface. For example, the convolutional network architecture may extract and generate deformation events such as tears, blunt dissection, cutting, suture breakage, bleeding, from the surface physical status (e.g., from determined strain and stress).

The MLMs 176 may be trained to be utilized via the machine learning engine 172 to determine a local, global, and/or dynamic response of the simulated soft body to the simulated force. The local response corresponds to one or more of the MLMs 176 determining static computation of the force displacement properties of the simulated soft body. In other words, the machine learning model determines a displacement of individual nodes included in the plurality nodes representing the simulated soft body in response to the simulated force. The local response is a point-wise interaction between the simulated force and one or more of the individual nodes included in the plurality of nodes. The global response corresponds to the same or a different one of the MLMs 176 determining a static computation of the force, stress, and/or strain distribution of each individual node included in the plurality of nodes of the simulated body (e.g., a response distribution map) based on the position of the nodes in the mesh. The dynamic response includes one or more of the MLMs 176 being given a sequence of inputs from the user (e.g., corresponding to the simulated force). The one or more MLMs then output (e.g., compute) the evolution of the system (e.g., the simulated soft body) over a period of time (e.g., until a static equilibrium state of the simulated soft body is reached). In some embodiments, the dynamic response may work in conjunction with the local and global response outputs for determining the dynamic response of the simulated soft body.

Training of the one or more MLMs 176 for determining the local, global, and dynamic response of the simulated soft body may be accomplished by utilizing a variety of techniques and data sources dependent on the desired state (e.g., volume deformation, strain, surface deformation, surface forces, and the like) of the simulated soft body. The data may be utilized to acquire the mechanical state of deformed soft bodies, which in turn may be utilized to train the one or more MLMs 176 to determine the previously described local, global, and dynamic response of the simulated soft body. In some embodiments, offline simulations (e.g., not real time) may provide a complete snapshot of the deformation of the soft body and corresponding strain for training of the one or more MLMs 176. In the same or other embodiments, video capture of real interactions may be used to compute surface deformations. Instrumented interaction (e.g., force sensors and the like) with animal models may also provide interaction force parameters and surface deformations. In some embodiments, elastometry, elastography, and other techniques may be used to measure strain inside animal models during deformation. In addition to video capture of real interactions, telemetry and/or haptics measurements may provide further datasets to be utilized in training the one or more MLMs 176. Thus, datasets from the video capture, instrumented interaction, elastometry, elastography, telemetry/haptics measurements, and other techniques may subsequently be utilized to train the one or more MLMs 176. In some embodiments, training with MLMs 176 with the described datasets (or others) may allow one or more of the MLMs 176 to visually represent aspects or features of the deformation without ever having an understanding of the underlying mechanical properties of the simulated soft body.

In some embodiments, the video annotation engine 174 may receive the simulated surgical videos from the video rendering engine 168 or the data store 160. The video annotation engine 170 may then annotate the simulated surgical video corresponding to the simulated surgical scenario including the simulated soft body. Annotating the simulated surgical videos may include directly altering the data of image frames from the simulated surgical videos, adding annotated metadata, generating an overlay to be superimposed on the simulated surgical video, or otherwise. In one embodiment, the video annotation engine 174 may assign metadata to groups of image pixels from corresponding image frames of the simulated surgical videos as representing the surgical instrument (e.g. real or simulated), while other groups of image pixels may have different metadata assigned indicating that the other groups of image pixels correspond to a certain anatomical region. Once annotation is complete, the video annotation engine 174 may store the simulated surgical videos (e.g., along with the associated metadata and/or labels) within the data store 160.

Figure 2A:
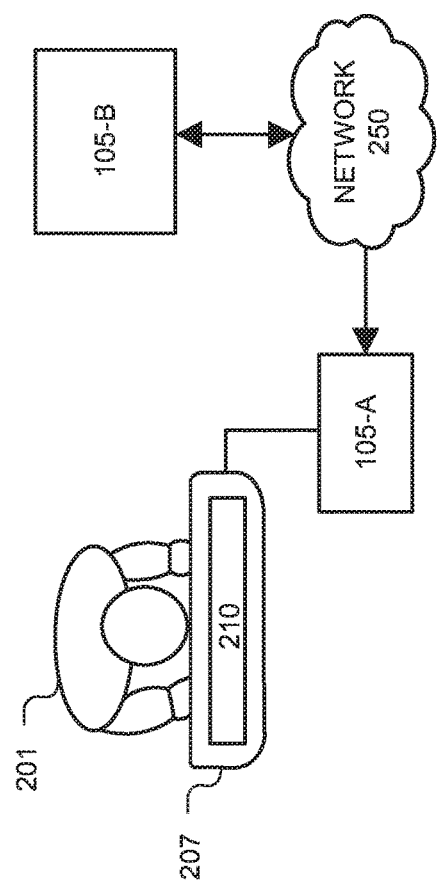
FIG. 2A illustrates a surgical simulator that incorporates features from the soft body simulator of FIG. 1, in accordance with an embodiment of the present disclosure.
Figure 2B:
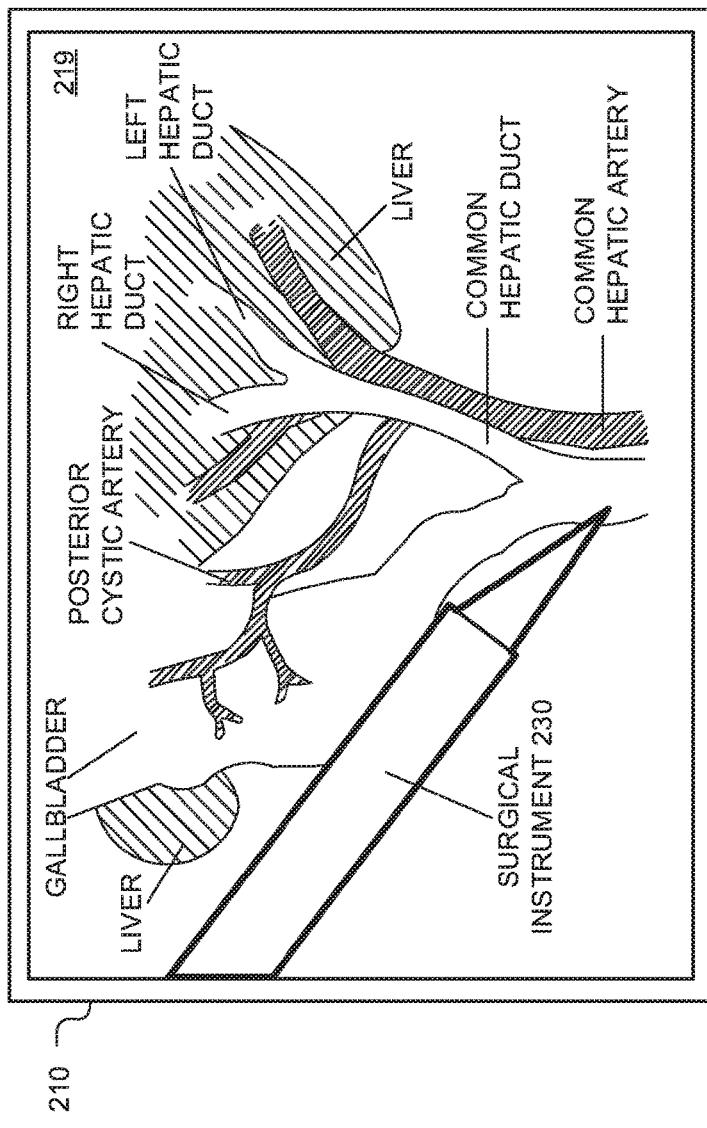
FIG. 2B illustrates an example control console and display of the surgical simulator in FIG. 2A, in accordance with an embodiment of the present disclosure.
Figure 2B:
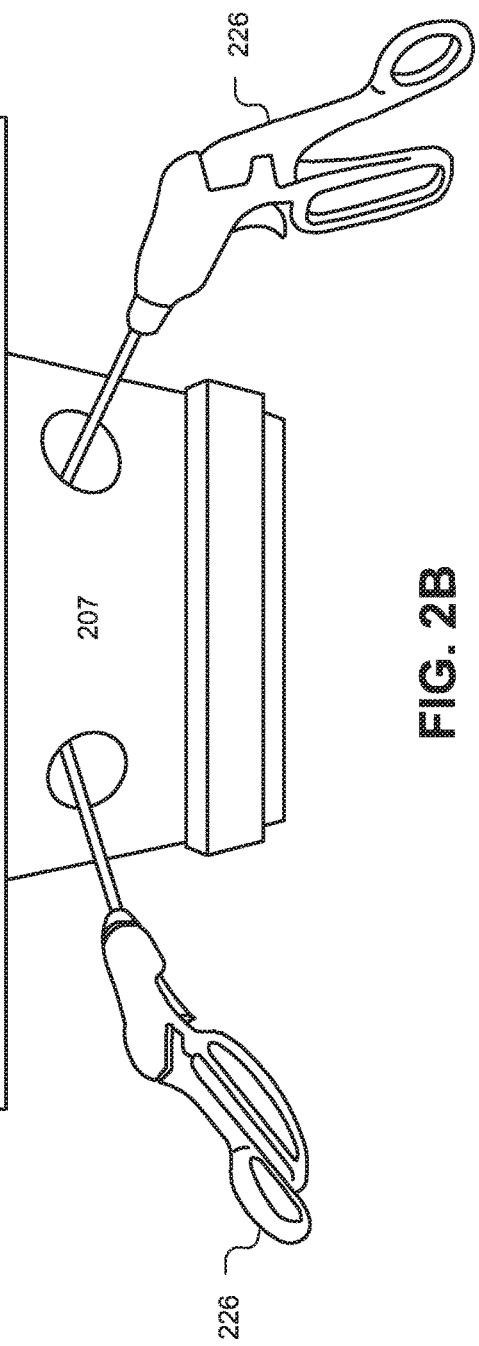

FIGS. 2A-2B illustrate a surgical simulator 200 that incorporates features from the soft body simulator 101 of FIG. 1, in accordance with an embodiment of the disclosure. Surgical simulator 200 is one possible implementation of soft body simulator 101 illustrated in FIG. 1. In the illustrated embodiment, the surgical simulator 200 is a virtual simulator that allows for the user to interact with a simulated soft body in a simulated environment. The surgical simulator 200 includes several input devices which may be included with or correspond to the user interfaces 115 of FIG. 1. As illustrated, these input devices include control console 207 and manipulators 226. The surgical simulator 200 may simulate performing a surgical procedure of a surgical scenario in a simulated environment that is shown to the user via display 210, which may correspond to the display system 110 of FIG. 1.

In the illustrated embodiment of FIG. 2A, the controller 105 is adapted to choreograph the operations and interaction between the components of the surgical simulator 200. Components of the controller 105 may be distributed locally (e.g., the controller 105-A) or coupled to the surgical simulator 200 remotely (e.g., the controller 105-B) via network 250.

FIG. 2B illustrates an example control console 207 and display 210 of the surgical simulator 200 of FIG. 2A, in accordance with an embodiment of the disclosure. As illustrated, the control console 207 includes manipulators 226, which in response to a physical action of the user, control a simulated surgical instrument of the simulated environment. More specifically, the manipulators 226 may include triggers, buttons, levers, and the like for controlling the simulated surgical instrument. This allows for the surgical simulator 200 to correlate a physical action of the user with a simulated action of the surgical simulator 200. Thus, in the simulated environment, the user may apply a simulated force to the simulated soft body. The display 210 is outputting an image frame 219 from the simulated surgical video corresponding to the simulation. In some embodiments, the image frame 219 may include an overlay which annotates elements of the image frame 219. In the illustrate embodiment, the annotations include labels identifying specific anatomical regions (e.g., liver, common hepatic duct, etc.), the surgical instrument 230, and the like. Elements may further be annotated by a border with pixel level accuracy of the simulated surgical video.

Figure 3A:
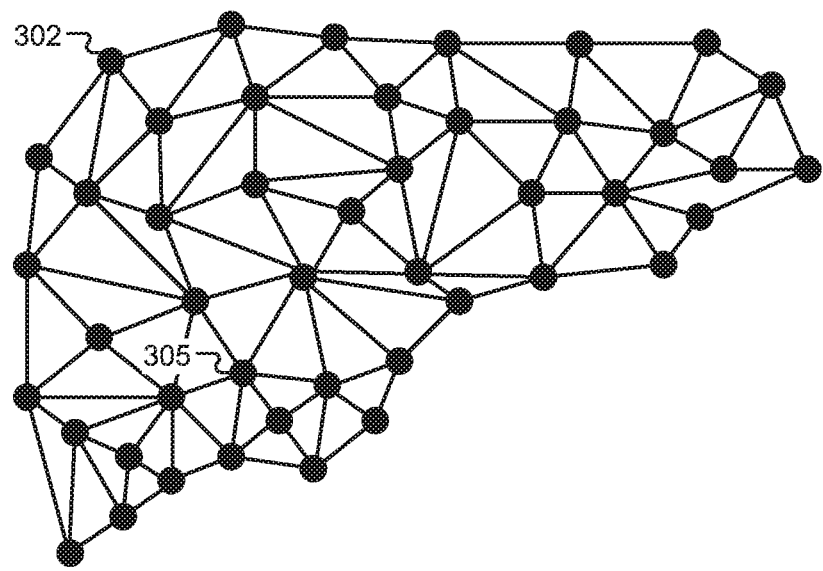
FIGS. 3A-3C illustrate an example rendering of a simulated soft body having a shape represented, at least in part, by a plurality of nodes, in accordance with an embodiment of the present disclosure.
Figure 3B:
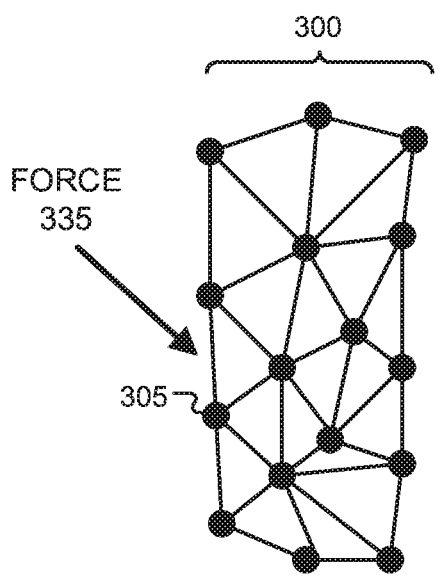
Figure 3C:
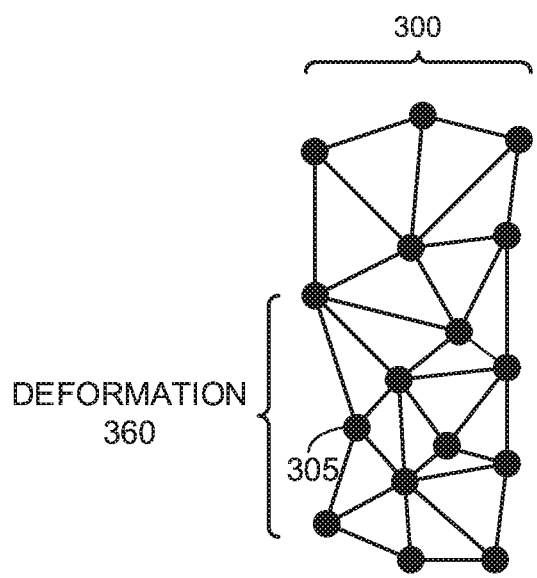

FIGS. 3A-3C illustrate an example rendering of a simulated soft body 300 having a shape represented, at least in part, by a plurality of nodes 302 including individual node 305. The simulated soft body 300 is one possible output of the soft body simulator (e.g., soft body simulator 101 of FIG. 1) that has been generated (e.g., via simulation engine 164 of FIG. 1). In the illustrated embodiment, the plurality of nodes 302 represents a simulated liver that a user may interact with via the soft body simulator (e.g., the soft body simulator 101 of FIG. 1). Deformation of the simulated soft body 300 in response to the interaction may be managed by one or more machine learning models (e.g., the MLMs 176 of FIG. 1). It is appreciated that in the illustrated embodiments the simulated soft body 300 is depicted as a wireframe model including the plurality of nodes 302. However, when rendered and output to a display (e.g., via the display system 110 of FIG. 1) for viewing by the user, the simulated soft body may include textures (e.g., via the asset management engine 166 of FIG. 1) to present a more realistic rendering of the simulated soft body (e.g., corresponding to a simulated liver).

FIG. 3A illustrates an anterior view of the simulated soft body 300 representing a simulated liver. As illustrated, the simulated soft body 300 includes a plurality of nodes 302, which together form the shape of the simulated soft body 300. In the illustrated embodiment, the simulated soft body 300 is depicted as a single resolution mesh polygon. However, it is appreciated that in other embodiments, the simulated soft body 300 may be a multi-resolution mesh polygon. In other words, the quantity of the individual nodes included in the plurality of nodes of the simulated soft body 300 may be a variable rather than a constant depending on the desired resolution of the simulated soft body 300.

In one embodiment, the simulated soft body 300 may include a low resolution representation, a medium resolution representation, and a high resolution representation. One difference between the low resolution representation, the medium resolution representation, and the high resolution representation is the quantity of the plurality of nodes. For example, the high resolution representation has a larger quantity of plurality of nodes than the medium resolution representation and the low resolution representation. The medium resolution representation has a larger quantity of the plurality of nodes than the low resolution representation and a smaller quantity of the plurality of nodes than the high resolution representation. Similarly, the low resolution representation has a smaller quantity of the plurality of nodes than the medium resolution representation and the high resolution representation. It is appreciated that the specific quantities of the plurality of nodes may be arbitrarily chosen based on variables such as computational cost, rendering time, and the like. In some embodiments, the multi-resolution mesh polygon may be determined by subsampling the high resolution representation to obtain lower resolution representations which are less computationally expensive to render. In some embodiments, MLM at different resolutions are combined, for example, if simulating certain aspects doesn't require the same granularity as simulating other aspects. In some embodiments, the multiple resolutions of the simulated soft body 300 may be utilized for training the one or more machine learning models via multi-objective optimization. Each of the resolutions may correspond to an objective of one of the machine learning models. In some embodiments, the multi-resolution representations may be utilized during the simulated to save on computational cost. For example, during the simulation parts (e.g., fovea, where the surgeon is looking) may be rendered at higher resolution while other parts (e.g., periphery) may be rendered at lower resolution.

FIG. 3B illustrates a cross-sectional view of the simulated soft body 300. As illustrated, a simulated force 335 is being applied to the simulated soft body 300. The simulated force corresponds to a physical action of a user (e.g., via one or more manipulators 226 of the surgical simulator 200 in FIG. 2A). In some embodiments, the soft body simulator (e.g., via physics engine 170 of FIG. 1) will calculate a point force applied to the plurality of nodes based on the simulated force 335 applied to the simulated soft body 300. The point force and corresponding node position for each of the plurality of nodes may then be inputted into a first machine learning model (e.g., from MLMs 176) to determine a displacement (e.g., a change in position) of individual nodes included in the plurality of nodes in response to the simulated force 335 being applied to the simulated soft body 330. Thus, the first machine learning model may be utilized to calculate the displacement of the individual nodes based, at least in part, on the inputted point force corresponding to the simulated force 335. The displacement of the individual nodes in response to the simulated force 330 may correspond to a local response of the simulated soft body 300 of the soft body simulator (e.g., the soft body simulated 101 of FIG. 1). The local response is a point-wise interaction between the simulated force 335 and one or more of the individual nodes included in the plurality of nodes of the simulated soft body 330.

FIG. 3C illustrates a cross-sectional view of the simulated soft body 300 after the simulated force 335 has been applied to the simulated soft body 300. More specifically, FIG. 3C illustrates rendering a deformation 360 of the simulated soft body 300 in substantially real time in response to the simulated force 335 based, at least in part on the displacement determined with the first machine learning model. As illustrated the displacement (e.g., change in position of node 305 relative to FIG. 3B and FIG. 3C) is induced by the simulated force 335. In some embodiments, the first machine learning model outputs the displacement of the individual nodes included in the plurality of nodes for at least one of the low resolution representation, the medium resolution representation, or high resolution representation of the simulated soft body 300 that is deformed in response to the simulated force. In the same or other embodiments, there could be temporal instances where a variety of resolutions of the simulated soft body are combined and/or superimposed.

However, the simulated force 335 and/or the deformation 360 of the simulated soft body 300 may result in a reaction force (e.g., compressive force), stress, and/or strain applied to the individual nodes of the simulated soft body 330 which may result in an unstable state of the simulated soft body 300. Thus, in order to reach a static equilibrium state, the deformation of the simulated soft body 300 may change to minimize the existing reaction force, stress, of strain caused by the deformation. For example, in one embodiment, after the simulated force 335 is removed from the simulated soft body 300, the deformation may change such that the plurality of nodes of the simulated soft body 300 return to their original positions (e.g., the position of the individual nodes before the simulated force 335 was applied to the simulated soft body 300). In other embodiments, the individual nodes of the simulated soft body 300 may not return to the exact same position (e.g., in situations where the stress/strain extends beyond the yield point of the simulated soft body 300). In some embodiments, the surgical scenario is related to neurological and/or musculoskeletal procedures and it may be advantageous to include a constraint reference frame. The one or more machine learning models may include additional inputs such as a reference (physical) frame that is fixed and used as a constraint.

To determine the state of the simulated soft body 300 based on the displacement (e.g., deformation) of the individual nodes included in the simulated soft body 300, one or more machine learning models (e.g., from the MLMs 176 of FIG. 1) may be utilized. In one embodiment, a second machine learning model is utilized to determine a response distribution map of the simulated soft body 300 based, at least in part, on the displacement. The response distribution map includes at least one of a reaction force, a stress, or a strain for each of the plurality of nodes of the simulated soft body 300. The response distribution map may correspond to a global response of the simulated soft body 300. In some embodiments, a dynamic simulation of the soft body may be generated in response to the reaction force, stress, and/or strain distribution of the simulated soft body 300 by integrating the equations of motion into the system (e.g., the soft body simulator 101 of FIG. 1) to determine, for example, velocity of individual nodes.

In the same or other embodiments, a third machine learning model may be utilized to dynamically generate the deformation of the simulated soft body 300 over a first time period based, at least in part, on the response distribution map. This may correspond to a dynamic response of the soft body simulator (e.g., the soft body simulator 101 of FIG. 1) in which a sequence of inputs from the user (e.g., corresponding to the simulated force 335) is input into the one or more machine learning models (e.g., the first machine learning model, the second machine learning model, and/or the third machine learning model). The one or more machine learning models then output (e.g., compute) the evolution of the system (e.g., deformation of the simulated soft body 300) over a period of time (e.g., until a static equilibrium state of the simulated soft body is reached).

Figure 4:
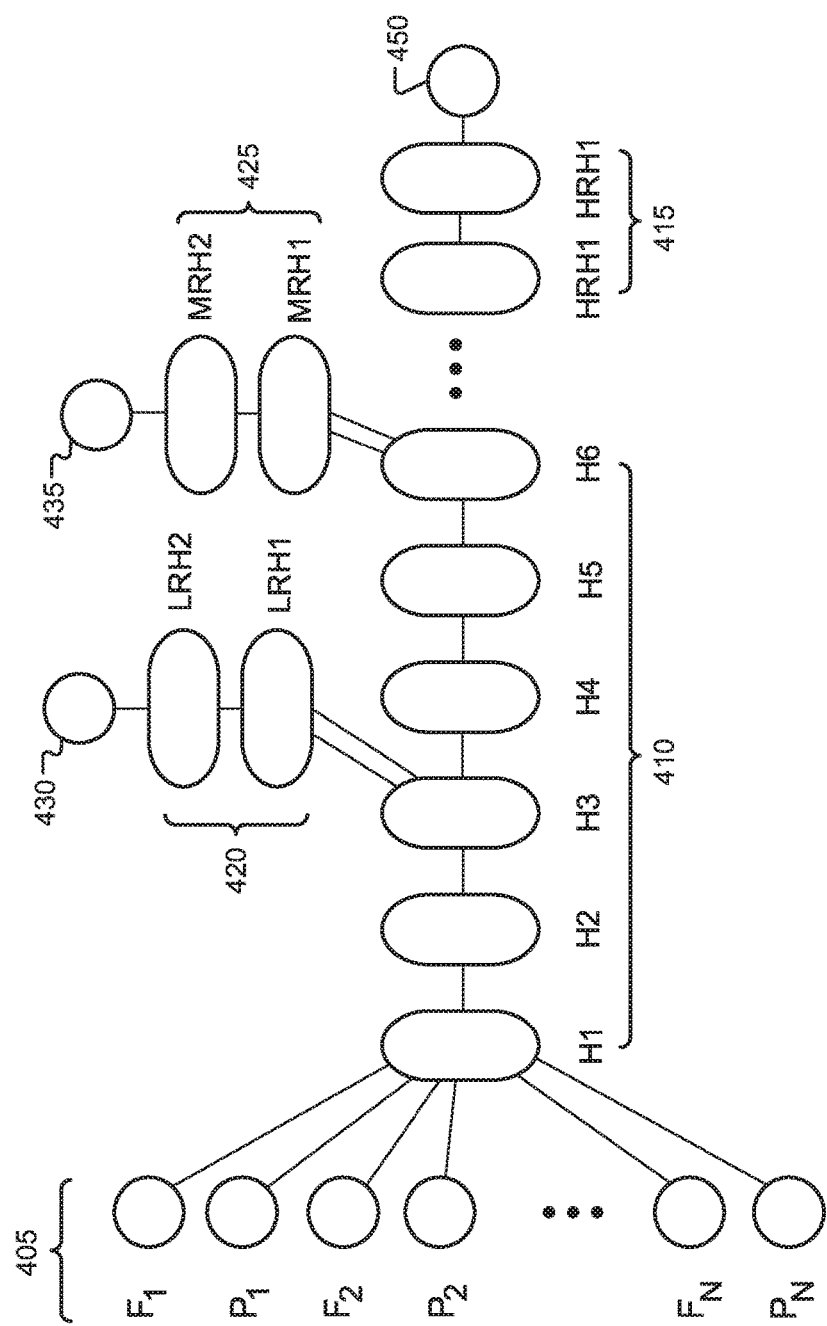
FIG. 4 illustrates an example machine learning model with a feed-forward deep neural network, in accordance with an embodiment of the present disclosure.

FIG. 4 illustrates an example machine learning model 400 with a feed-forward deep neural network, in accordance with an embodiment of the present disclosure. The machine learning model 400 may correspond to the previously described first machine learning model utilized to determine the displacement of the simulated soft body in response to the simulated force being applied to the simulated soft body. In other words, the machine learning model 400 is one possible neural network that may be implemented for determining a local response of the simulated soft body.

As illustrated, the machine learning model 400 is a multi-layer deep neural network with a single tower that has been trained via multi-objective optimization to determine the displacement of the simulated soft body. The machine learning model 400 includes a plurality of inputs 405 (e.g., $F_1$, $P_1$, $F_2$, $P_2$, etc.) for force and position (e.g., magnitude and direction of force applied to individual nodes at specific positions). The force, for example, may correspond to a point force applied to the plurality of nodes based on the simulated force applied to the simulated soft body. Along the single tower of the machine learning model 400 are hidden layers 410 (e.g., $H_1$, $H_2$, $H_3$, etc.). Some hidden layers (e.g., low resolution hidden layers 420, medium resolution hidden layers 425, and high resolution hidden layers 415, respectively) may be specific to objectives which output the displacement for low resolution (e.g., output 430), medium resolution (e.g., output 435), and high resolution (e.g., output 450) representations of the simulated soft body.

The multiple objectives may facilitate training the machine learning model 400. For example, hidden layers H1-H3 may have parameters and weights set initially based on the low resolution representation of the simulated soft body, which may be computationally less costly relative to medium or high resolution representations. Similarly, the training of the machine learning model 400 may continue with the medium resolution representation which may further tune the hidden layers 410 at less computational cost relative to the high resolution representation. Thus, in some embodiments, the machine learning model 400 may be trained to determine the displacement of individual nodes with the simulated soft body generated at different resolutions (e.g., low resolution representation, medium resolution representation, and high resolution representation). As illustrated the machine learning model 400 includes a first objective (e.g., output 430) associated with the low resolution, a second objective (e.g., output 435) associated with the medium resolution, and a third objective (e.g., output 450) associated with the third object along the single tower of the machine learning model 400. As illustrated, the second objective is positioned between the first objective and the third objective along the single tower of the machine learning model 400. The machine learning model 400 may subsequently output the displacement of the individual nodes included in the plurality of nodes of the simulated soft body for at least one a low resolution representation, a medium resolution representation, or a high resolution representation of the simulated soft body being deformed in response to the simulated force.

Figure 5A:
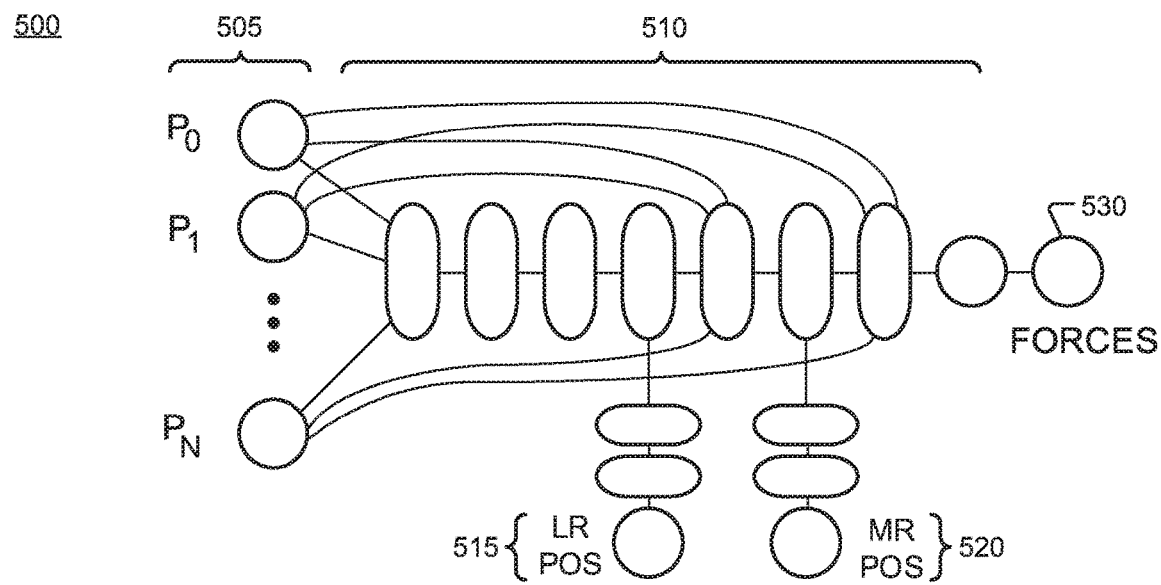
FIGS. 5A-5B illustrates an example machine learning model with a feed-forward deep neural network, in accordance with embodiments of the present disclosure.
Figure 5B:
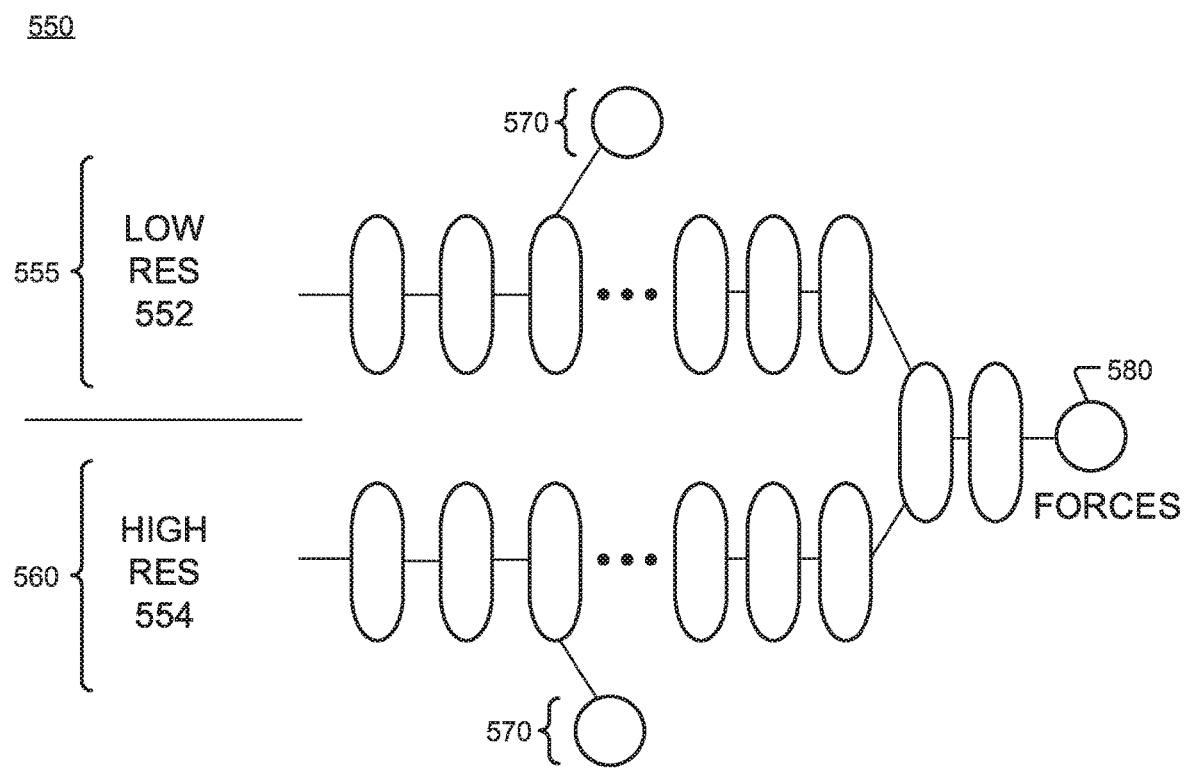

FIGS. 5A-5B illustrate an example machine learning model with a feed-forward deep neural network, in accordance with embodiments of the present disclosure. More specifically, the machine learning model 500 of FIG. 5A and the machine learning model 550 of FIG. 5B may correspond to the previously described second machine learning model utilized to determine the response distribution map of the simulated soft body. Thus, the machine learning models 500 and 550 are possible neural networks that may be implemented for determining a global response of the simulated soft body.

FIG. 5A illustrates machine learning model 500 that is a multi-layer deep neural network trained via multi-objective optimization based, at least in part, on the displacement of at least one of the low resolution representation, the medium resolution representation, or the high resolution representation of the simulated soft body. As illustrated the machine learning model 500 is a single tower neural network that includes a plurality of inputs 505 to receive position (e.g., $P_0$, $P_1$, etc.) of each of the individual nodes included in the plurality of nodes of the simulated soft body. The machine learning model 500 also includes a plurality of hidden layers 510, a first objective 515 associated with a low resolution representation of the simulated soft body, a second objective 520 associated with a medium resolution representation of the simulated soft body, and an output 530. The output 530 of the machine learning model 500 computes the force distribution map (e.g., the force, stress, and/or strain at each of the individual nodes included in the plurality of nodes of the simulated soft body).

FIG. 5B illustrates machine learning model 550 that is a multi-layer deep neural network including a first tower 555 associated with the low resolution representation of the simulated soft body and a second tower 560 associated with the high resolution representation of the simulated soft body. The machine learning model 550 also includes break outs 570 associated with objectives for the medium resolution representation of the simulated soft body. The machine learning model 550 receives inputs 552 and 554 for low resolution and high resolution representations, respectively, for the position of individual nodes of the simulated soft body and in response outputs 580 for the associated forces (e.g., the force distribution map included at least one of a reaction force, stress, or strain for each one of the individual nodes of the simulated soft body) of the simulated soft body based on the node position.

Figure 6:
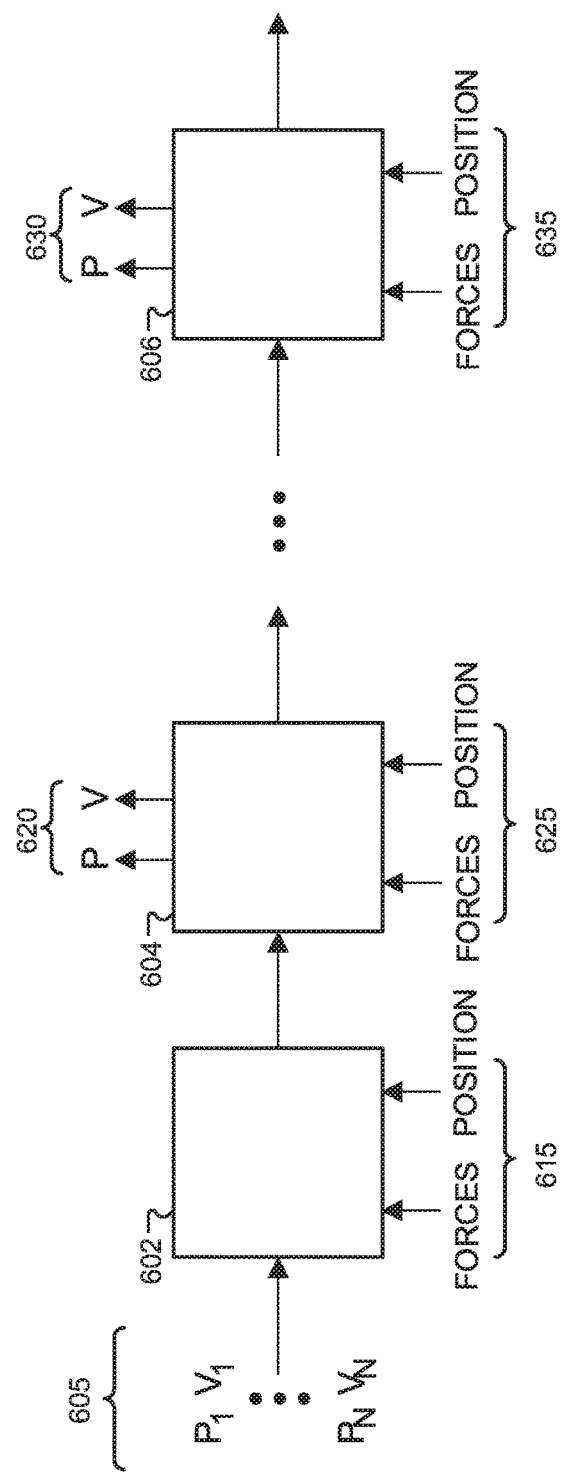
FIG. 6 illustrates an example machine learning model with a recurrent neural network, in accordance with an embodiment of the present disclosure.

FIG. 6 illustrates an example machine learning model 600 with a recurrent neural network, in accordance with an embodiment of the present disclosure. More specifically, the machine learning model 600 may correspond to the previously described third machine learning model utilized to dynamically generate the deformation of the simulated soft body over a first period of time based, at least in part, on the response distribution map. Thus, the machine learning model 600 is a possible neural network that may be implemented for determining the dynamic response of the simulated soft body to the simulated force.

As illustrated, the machine learning model 600 includes a plurality of states (e.g., states 602, 604, 606, etc.). For example state 602 corresponds to an initial or first state of the machine learning model 600. The initial state 602 of the machine learning model 600 receives inputs for initial velocity/position 605 of each of the plurality of nodes included in the simulated soft body as well as force/position (e.g., the response distribution map) for each of the plurality of nodes. The machine learning model 605 then generates an updated response distribution map 625, velocity 620, and associated position for each of the plurality of nodes, which are subsequently input into the next sequential state 604. Thus, the machine learning model 600 updates the plurality of states sequentially based, at least in part, on the updated response distribution map and the velocity of the previous state of the machine learning model 600. The sequential updating of the states of the machine learning model 600 is utilized to compute the evolution of the system (e.g., the simulated soft body) over a period of time (e.g., until a static equilibrium state of the simulated soft body is reached).

Figure 7:
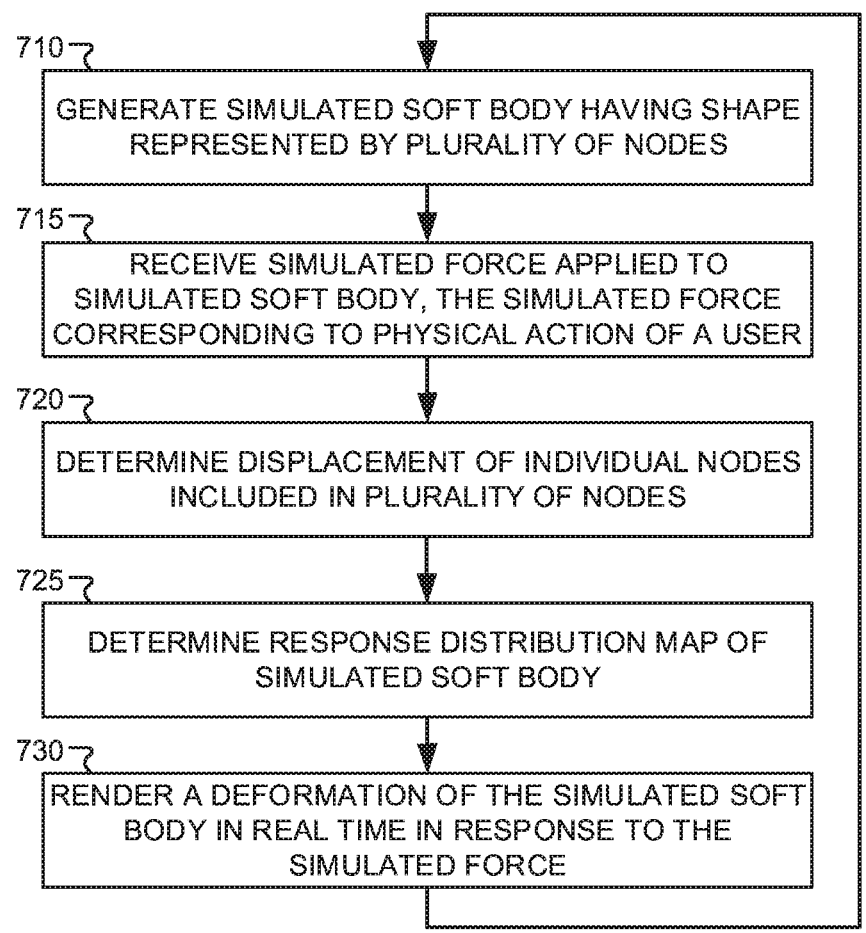
FIG. 7 illustrates a method for generating a simulated soft body and rendering a deformation of the simulated soft body in real time in response to a simulated force, in accordance with an embodiment of the present disclosure.

FIG. 7 illustrates a method 700 of generating a simulated soft body and rendering a deformation of the simulated soft body in real time in response to a simulated force, in accordance with an embodiment of the present disclosure.

Block 710 illustrates generating a simulated soft body having a shape represented, at least in part, by a plurality of nodes. The simulated soft body may be generated by a soft body simulator, a surgical simulator, and the like (e.g., soft body simulator 101 of FIG. 1). In some embodiments, the simulated soft body is a multi-resolution mesh polygon including a low resolution representation, a medium resolution representation, and a high resolution representation.

Block 715 shows receiving a simulated force applied to the simulated soft body. The simulated force corresponds to a physical action of the user. For example, in one embodiment the user may utilize manipulators (e.g., manipulators 226 of FIG. 2A) to correlate a physical motion to the simulated force. During the simulation, the user may apply simulated force to the simulated soft body. In some embodiments, a point force applied to the plurality of nodes based on the simulated force is calculated to determine the force magnitude and direction applied to individual nodes included in the plurality of nodes.

Block 720 illustrates determining the displacement of individual nodes included in the plurality of nodes in response to the simulated force applied to the simulated soft body. The determined displacement may correspond to a local response of the simulated soft body. In some embodiments, the displacement is determined, at least in part, with a first machine learning model. Determining the displacement may include inputting the calculated point force and corresponding node position for each of the plurality of nodes into the first machine learning model. Then, with the first machine learning model, the displacement of the individual nodes included in the plurality of nodes may be calculated based, at least in part, on the point force. In some embodiments the first machine learning model is a multi-layer deep neural network with a single tower that is trained, at least in part, via multi-objective optimization to determine the displacement. In the same or other embodiments, the first machine learning model may be trained before inputting the point force.

The first machine learning model may be trained to determine the displacement of the individual nodes with the simulated soft body generated at different resolutions. The different resolutions may include a low resolution, medium resolution, and high resolution representations of the simulated soft body. The first machine learning model includes a first objective associated with the low resolution, a second objective associated with the medium resolution, and a third objective associated with the high resolution representations respectively. The second objective may be positioned between the first objective and the third objective along the single tower of the first machine learning model. In some embodiments, the first machine learning model may output the displacement of the individual nodes included in the plurality of nodes for at least one of the low resolution, the medium resolution, or the high resolution representation of the simulated soft body being deformed in response to the simulated force.

Block 725 shows determining a response distribution map of the simulated soft body. The response distribution map may correspond to a global response of the simulated soft body to the simulated force. The response distribution map may be based, at least in part, on the displacement, and includes at least one of a reaction force, a stress, or a strain for each of the plurality of nodes of the simulated soft body. In some embodiments, the response distribution map is determined by inputting the displacement into a second machine learning model. The second machine learning model may be a multi-layer deep neural network trained via multi-objective optimization based on the displacement of the low resolution, medium resolution, and high resolution representation of the simulated soft body.

In other embodiments, the second machine learning model is a multi-layer deep neural network including a first tower associated with the low resolution representation of the simulated soft body and a second tower associated with the high resolution representation of the simulated soft body. In some embodiments a high resolution representation of the simulated soft body being deformed in response to the simulated force is generated and subsequently rendered. The high resolution representation may be subsampled to generate the low resolution representation. The node position of the low resolution representation and the high resolution representation may be input into the first tower and second tower of the second machine learning model respectively to calculate at least one of the reaction force, stress, or stress (e.g., the response distribution map) for each of the plurality of nodes based, at least in part, on the displacement of the nodes.

Block 730 illustrates rendering a deformation of the simulated soft body in substantially real time in response to the simulated force. The real time rendering of the deformation may be a dynamic response of the simulated soft body in response to the simulated force based, at least in part, on the displacement. In the same or other embodiments, the dynamic response of the simulated soft body to the simulated force may be determined. In one embodiment, deformation of the simulated soft body over a first period of time may be dynamically generated with a third machine learning model based, at least in part, on the response distribution map. The third machine learning model may be a recurrent neural network including a plurality of states. The third machine learning model may receive inputs including the response distribution map and an initial velocity associated with an initial state included in the plurality of states. Then, via the third machine learning model, an updated response distribution map and a velocity for each of the plurality of states other than the initial state may be generated. Each of the plurality states may be updated sequentially and be based, at least in part, on the updated response distribution map and the velocity of the previous state.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise. It is appreciated that terms like "a surgical robot" or "robot-assisted surgery" may include any system that aids or assists in surgery (e.g., a virtual assistant), and does not actually have to perform the surgery or have moving parts.

Some portions of the detailed description are presented in terms of algorithms and symbolic representations of operations on data bits within a computer memory. These algorithmic descriptions and representations are used by those skilled in the data processing arts to effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "generating", "receiving", "determining", "rendering", "calculating", "training", "subsampling", "transforming", "correlating" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission, or display devices.

Embodiments described herein relate to an apparatus for performing the operations herein. This apparatus may be specially constructed for the specified purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A tangible machine-readable storage medium includes any mechanism that provides (i.e., stores) information in a non-transitory form accessible by a machine or controller (e.g., a computer, network device, personal digital assistant, manufacturing tool, any device with a set of one or more processors, general-purpose processor configured by firmware/software, programmable gate array, or application specific integrated circuit, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for simulating soft body deformation, the method comprising:
   generating a simulated soft body having a shape represented, at least in part, by a plurality of nodes;
   transforming a physical action of a user received at a user interface into a simulated force to apply to the simulated soft body;
   determining, with at least a first machine learning model, a displacement of individual nodes included in the plurality of nodes in response to the simulated force applied to the simulated soft body, wherein the first machine learning model is a neural network including one or more hidden layers associated with both a first objective output and a second objective output, wherein the first objective output and the second objective output respectively provide the displacement for different resolution representations of the simulated soft body; and
   rendering a deformation of the simulated soft body for at least one of the different resolution representations of the simulated soft body in response to the simulated force based, at least in part, on the displacement.

2. The method of claim 1, further comprising:
calculating a point force applied to the plurality of nodes based on the simulated force applied to the simulated soft body;
inputting the point force and a node position for each of the plurality of nodes into the first machine learning model; and
calculating, with the first machine learning model, the displacement of the individual nodes included in the plurality of nodes based, at least in part, on the point force.

3. The method of claim 1, wherein the first machine learning model is a multi-layer deep neural network, and wherein the first machine learning model is trained, at least in part, via multi-objective optimization to determine the displacement in real time.

4. The method of claim 3, further comprising:
training the first machine learning model to determine the displacement of the individual nodes with the simulated soft body generated at the different resolutions, wherein the different resolutions include a low resolution, a medium resolution, and a high resolution of the simulated soft body, each associated with a different quantity of the plurality of nodes, wherein the first machine learning model includes a first objective associated with the low resolution, a second objective associated with the medium resolution, and a third objective associated with the high resolution, wherein the first objective output is associated with the low resolution and the second objective output is associated with the medium resolution or the high resolution, and wherein the second objective is positioned between the first objective and the third objective.

5. The method of claim 1, further comprising:
outputting, with the first machine learning model, the displacement of the individual nodes included in the plurality of nodes at each of the different resolution representations of the simulated soft body being deformed in response to the simulated force.

6. The method of claim 5, further comprising:
determining, with a second machine learning model, a response distribution map of the simulated soft body based, at least in part, on the displacement, wherein the response distribution map includes at least one of a reaction force, a stress, or a strain for each of the plurality of nodes of the simulated soft body.

7. The method of claim 6, wherein the second machine learning model is a multi-layer deep neural network trained via multi-objective optimization based on the displacement of the different resolution representations of the simulated soft body.

8. The method of claim 6, wherein the second machine learning model is a multi-layer deep neural network including a first tower associated with a low resolution representation of the simulated soft body included in the different resolution representations, and a second tower associated with the high resolution representation of the simulated soft body included in the different resolution representations.

9. The method of claim 8, further comprising:
rendering the high resolution representation of the simulated soft body being deformed in response to the simulated force;
subsampling the deformed soft body to generate the low resolution representation;
inputting the low resolution representation into the first tower and the high resolution into the second tower; and
calculating at least one of the reaction force, the stress, or the strain for each of the plurality of nodes based, at least in part, on the displacement of nodes included in the low resolution representation and the high resolution representation.

10. The method of claim 6, further comprising:
generating, with a third machine learning model, the deformation of the simulated soft body over a first period of time based, at least in part, on the response distribution map.

11. The method of claim 10, wherein the third machine learning model is a recurrent neural network (RNN) including a plurality of states, wherein the method further includes:
receiving inputs including the response distribution map and an initial velocity associated with an initial state included in the plurality of states of the RNN; and
generating an updated response distribution map and a velocity for each of the plurality of states other than the initial state, wherein each of the plurality of states are updated sequentially and is based, at least in part, on the updated response distribution map and the velocity of the previous state of the RNN.

12. A simulator for simulating soft body deformation, the simulator comprising:
a display system adapted to show a rendering of a simulated soft body to a user of the simulator;
a user interface adapted to receive a physical action of the user; and
a controller including one or more processors coupled to memory, the display system, and the user interface, wherein the memory stores instructions that when executed by the one or more processors cause the simulator to perform operations including:
generating the simulated soft body having a shape represented, at least in part, by a plurality of nodes;
correlating the physical action of the user to a simulated force applied to the simulated soft body;
determining, with at least a first machine learning model, a displacement of individual nodes included in the plurality of nodes in response to the simulated force applied to the simulated soft body, wherein the first machine learning model is a neural network including one or more hidden layers associated with both a first objective output and a second objective output, wherein the first objective output and the second objective output respectively provide the displacement for different resolution representations of the simulated soft body; and
rendering a deformation of the simulated soft body for at least one of the different resolution representations of the simulated soft body in response to the simulated force based, at least in part, on the displacement.

13. The simulator of claim 12, wherein the controller includes additional instructions that when executed by the one or more processors cause the simulator to perform further operations comprising:
calculating a point force applied to the plurality of nodes based on the simulated force applied to the simulated soft body;
inputting the point force and node position for each of the plurality of nodes into the first machine learning model; and
calculating, with the first machine learning model, the displacement of the individual nodes included in the plurality of nodes based, at least in part, on the point force.

14. The simulator of claim 12, further comprising:
a machine learning model (MLM) database coupled to the controller, wherein the MLM database includes the first machine learning model, wherein the first machine learning model is a multi-layer deep neural network, and wherein the first machine model is trained, at least in part, via multi-objective optimization to determine the displacement.

15. The simulator of claim 14, wherein the controller includes additional instructions that when executed by the one or more processors cause the simulator to perform further operations including:
training the first machine learning model to determine the displacement of the individual nodes with the simulated soft body generated at the different resolutions, wherein the different resolutions include a low resolution, a medium resolution, and a high resolution of the simulated soft body, each associated with a different quantity of the plurality of nodes, wherein the first machine learning model includes a first objective associated with the low resolution, a second objective associated with the medium resolution, and a third objective associated with the high resolution, wherein the first objective output is associated with the low resolution and the second objective output is associated with the medium resolution or the high resolution, and wherein the second objective is positioned between the first objective and the third objective.

16. The simulator of claim 12, wherein the controller includes additional instructions that when executed by the one or more processors cause the surgical simulator to perform further operations including:
outputting, with the first machine learning model, the displacement of the individual nodes included in the plurality of nodes for the different resolution representations of the simulated soft body being deformed in response to the simulated force; and
determining, with a second machine learning model, a response distribution map of the simulated soft body based, at least in part, on the displacement, wherein the response distribution map includes at least one of a reaction force, a stress, or a strain for each of the plurality of nodes of the simulated soft body.

17. The simulator of claim 16, wherein the MLM database includes the second machine learning model, and wherein the second machine learning model is a multi-layer deep neural network trained via multi-objective optimization based on the displacement of the different resolution representations of the simulated soft body.

18. The simulator of claim 16, wherein the MLM database includes the second machine learning model, wherein the second machine learning model is a multi-layer deep neural network including a first tower associated with a low resolution representation of the simulated soft body included in the different resolution representations, and a second tower associated with a high resolution representation of the simulated soft body included in the different resolution representations.

19. The simulator of claim 18, wherein the controller includes additional instructions that when executed by the one or more processors cause the surgical simulator to perform further operations including:
rendering the high resolution representation of the simulated soft body being deformed in response to the simulated force;
subsampling the deformed soft body to generate the low resolution representation;
inputting the low resolution representation into the first tower and the high resolution into the second tower; and
calculating at least one of the reaction force, the stress, or the strain for each of the plurality of nodes based, at least in part, on the displacement of nodes including in the low resolution representation and the high resolution representation.

20. The simulator of claim 16, wherein the controller includes additional instructions that when executed by the one or more processors cause the surgical simulator to perform further operations including:
generating, with a third machine learning model, the deformation of the simulated soft body over a first period of time based, at least in part, on the response distribution map, wherein the third machine learning model is a recurrent neural network (RNN) including a plurality of states;
receiving inputs including the response distribution map and an initial velocity associated with an initial state included in the plurality of states of the RNN; and
generating an updated response distribution map and a velocity for each of the plurality of states other than the initial state, wherein each of the plurality of states are updated sequentially and is based, at least in part, on the updated response distribution map and the velocity of the previous state of the RNN.

21. A non-transitory computer-readable storage medium having stored thereon instructions which, when executed by one or more processing units, cause the one or more processing units to perform operations comprising:
generating a simulated soft body having a shape represented, at least in part, by a plurality of nodes;
determining, with at least a first machine learning model, a displacement of individual nodes included in the plurality of nodes in response to a simulated force being applied to the simulated soft body, wherein the first machine learning model is a multi-layer deep neural network trained, at least in part, via multi-objective optimization to determine the displacement, wherein the first machine learning model is a neural network including one or more hidden layers associated with both a first objective output and a second objective output, wherein the first objective output and the second objective output respectively provide the displacement for different resolution representations of the simulated soft body; and
rendering a deformation of the simulated soft body for at least one of the different resolution representations of the simulated soft body in response to the simulated force based, at least in part, on the displacement.

22. The non-transitory computer-readable medium of claim 21, wherein the instructions, which when executed by the one or more processing units, cause the one or more processing units to perform further operations comprising:
outputting, with the first machine learning model, the displacement of the individual nodes included in the plurality of nodes for the different resolution representations of the simulated soft body being deformed in response to the simulated force; and
determining, with a second machine learning model, a response distribution map of the simulated soft body based, at least in part, on the displacement, wherein the response distribution map includes at least one of a reaction force, a stress, or a strain for each of the plurality of nodes of the simulated soft body.

23. The non-transitory computer-readable medium of claim 22, wherein the instructions, which when executed by the one or more processing units, cause the one or more processing units to perform further operations comprising:
generating, with a third machine learning model, the deformation of the simulated soft body over a first period of time based on, at least in part, the response distribution map.

24. The non-transitory computer-readable medium of claim 21, wherein the third machine learning model is a recurrent neural network (RNN) including a plurality of states, and wherein the instructions, which when executed by the one or more processing units, cause the one or more processing units to perform further operations comprising:
receiving inputs including the response distribution map and an initial velocity associated with an initial state included in the plurality of states of the RNN; and
generating an updated response distribution map and a velocity for each of the plurality of states other than the initial state, wherein each of the plurality of states are updated sequentially and is based, at least in part, on the updated response distribution map and the velocity of the previous state of the RNN.

* * * * *